United States Patent
Lu et al.

(10) Patent No.: US 7,988,696 B2
(45) Date of Patent: Aug. 2, 2011

(54) PERFORATED BALLOON AND METHOD FOR FORMING A HARDENED ORTHOPAEDIC PASTE IN A BONE USING SAME

(75) Inventors: Pong-Jeu Lu, Tainan (TW); Jiin-Huey Chern Lin, Winnetka, IL (US); Chien-Ping Ju, Carbondale, IL (US)

(73) Assignee: Joy Medical Devices Corporation, Kaohsiung (TW)

( * ) Notice: Subject to any disclaimer, the term of this patent is extended or adjusted under 35 U.S.C. 154(b) by 326 days.

(21) Appl. No.: 12/155,273

(22) Filed: Jun. 2, 2008

(65) Prior Publication Data

US 2008/0300604 A1    Dec. 4, 2008

Related U.S. Application Data

(63) Continuation-in-part of application No. 11/919,655, filed on Oct. 31, 2007.

(60) Provisional application No. 60/932,586, filed on Jun. 1, 2007.

(51) Int. Cl.
*A61B 17/58* (2006.01)
*A61B 17/60* (2006.01)
*A61F 2/00* (2006.01)

(52) U.S. Cl. .......... 606/94; 606/92; 604/96.01
(58) Field of Classification Search .......... 606/92–94; 604/96.01
See application file for complete search history.

(56) References Cited

U.S. PATENT DOCUMENTS

| 4,671,263 | A | 6/1987 | Draenert |
| 5,755,797 | A | 5/1998 | Baumgartner |
| 6,355,013 | B1 * | 3/2002 | van Muiden .......... 604/96.01 |
| 7,144,398 | B2 | 12/2006 | Lin et al. |
| 7,306,610 | B2 | 12/2007 | Lin et al. |
| 2002/0058947 | A1 | 5/2002 | Hochschuler et al. |
| 2003/0032964 | A1 | 2/2003 | Watkins et al. |
| 2004/0186481 | A1 * | 9/2004 | Chern Lin et al. .......... 606/92 |
| 2004/0196735 | A1 | 10/2004 | Barker et al. |
| 2005/0216025 | A1 | 9/2005 | Lin et al. |
| 2005/0222538 | A1 | 10/2005 | Embry et al. |
| 2005/0234498 | A1 | 10/2005 | Gronemeyer et al. |

* cited by examiner

*Primary Examiner* — Thomas C Barrett
*Assistant Examiner* — Andrew Yang
(74) *Attorney, Agent, or Firm* — Bacon & Thomas, PLLC

(57) ABSTRACT

The present invention discloses a technique for forming a hardened orthopaedic paste in a bone cavity, which involves a forced-feeding balloon rupture mechanism. This mechanism includes continuously or intermittently injecting a liquid or gas into a perforated balloon containing a hardened orthopaedic paste therein in a bone cavity until the perforated balloon is dilated to exceed a critical size, and thus ruptures.

9 Claims, 1 Drawing Sheet

US 7,988,696 B2

PERFORATED BALLOON AND METHOD FOR FORMING A HARDENED ORTHOPAEDIC PASTE IN A BONE USING SAME

CROSS-REFERENCE TO RELATED APPLICATION

The present application is a continuation-in-part application of U.S. patent application Ser. No. 11/919,655, filed Oct. 31, 2007, disclosure of which is incorporated herein by reference. This patent application claims the benefit under 35 USC 119 (e) of U.S. Provisional Patent Application No. 60/932,586, filed Jun. 1, 2007.

FIELD OF THE INVENTION

The present invention is related to a technique for forming a hardened orthopaedic paste in a bone by inserting a perforated balloon in the bone, injecting an orthopaedic paste into said balloon, which will harden in-situ, and rupturing the balloon to leave the hardened paste in the bone, acting as a medical implant. The orthopaedic paste can be any known flowable orthopaedic filling material including, for example, a liquid-powder mixture and a viscous liquid containing a polymeric material.

BACKGROUND OF THE INVENTION

It is well accepted that bioresorbable orthopedic implants are always the better choice than permanent foreign-body implants, as long as their bioresorption rates, biomechanical properties and variations in biomechanical properties with respect to the resorption processes are appropriately controlled. Among all bioresorbable orthopedic implants, calcium-based implants (calcium phosphate, calcium sulfate, etc), are perhaps the top choice so far.

For the purpose of filling a bone cavity, especially an irregularly-shaped bone cavity, a bone cement paste (for example, a PMMA, calcium phosphate cement or calcium sulfate cement) is often injected into the cavity, wherein the bone cement paste is hardened in-situ. This hardened cement will remain in bone as a permanent implant if it is a permanent foreign-body implant such as PMMA, or gradually replaced by natural bone if it is a bioresorbable material such as calcium phosphate or calcium sulfate. For load-bearing applications, this hardened cement should provide a sufficient strength to withstand the post-operation routine loadings.

Most conventional methods of forming a hardened (set) bone cement in bone cavity involve creating a bone cavity, followed by directly injecting a cement paste into the bone cavity. Such an approach suffers the following major drawbacks among others:

(1) Since the cement paste is directly injected into an environment filled with blood/body fluid, the cement particles are easily dispersed in this environment, especially before the paste is fully set. The dispersed cement particles can penetrate into surrounding tissues, cracks, blood vessels, nerve system, etc. and cause various kinds of clinical complications such as potentially fatal cement embolism.

(2) Since the cement paste is hardened in blood/body fluid, the predetermined liquid/powder ratio, which is critical to cement properties, is disrupted in-situ, causing the performance/properties of the cement to degrade. Although applying pressure to the cement during its hardening process can improve the cement strength, surgeons usually avoid applying a high pressure directly to the injected cement paste due to the above-mentioned potential risks of complications.

(3) Besides the disruption in liquid/powder ratio, the irregular shape of the hardened cement also decreases the biomechanical properties of the cement and increases the uncertainty/risks of the cement performance (depending on the actual shape and filling condition), especially for bioceramic cements such as calcium phosphate cement and calcium sulfate cement. The decreased strength further causes the cement to more easily disperse/disintegrate.

Another approach to inject an orthopedic implant into a bone cavity involves inserting a container (balloon or pocket) into the cavity; injecting a bone filler (not necessarily a hardenable cement paste) into the container through a tube; and separating the container from the tube with the container and its contained bone filler remaining in bone. One major problem with this approach is that the container left in bone becomes a permanent foreign body which prevents the bone filler from directly interacting with bone tissue to form a biological or even only a chemical or physical bond between the bone filler and bone. Furthermore, most popularly-used containers (balloons) are made from polymers which are not bioactive, bioconductive, or even biocompatible. The negative effects of this permanently implanted container are most obvious when the bone filler is a bioresorbable material, such as a calcium phosphate or calcium sulfate-based material. In this case even a biodegradable polymer container hinders the bioresorption process of the bioresorbable bone filler for a season, especially during the most critical early stage resorption/healing process. Furthermore, most biodegradable polymers do not demonstrate mechanical properties as desired.

An improved method for forming a hardened cement in a bone cavity involves inserting an inflatable, preferably inflatable and expandable, pocket into a bone being treated; injecting a hardenable cement paste into the pocket through a tube which connects and carries the pocket into the bone; allowing the cement paste to harden within the pocket in the bone cavity; opening the pocket; separating the pocket from the hardened cement, and retrieving the opened pocket from the bone with the hardened cement remaining in the bone. Advantages of this method include allowing the hardened cement implant to directly contact the surrounding bone tissue thus enhancing the healing process, and the much higher strength of the hardened cement compared to that of the cement paste directly injected into the bone cavity. This is especially advantageous for bioresorbable implants. A typical example can be found in U.S. Pat. No. 7,306,610 B2.

A further improved method for forming a hardened cement in a bone cavity involves inserting an inflatable, preferably inflatable and expandable, pocket into a bone being treated; injecting a hardenable cement paste into the pocket through a tube which connects and carries the pocket into the bone, therein said pocket is made from a material penetrable to liquid but substantially impenetrable to the powder of said cement paste; allowing the cement paste to harden within the pocket in the bone cavity; opening the pocket; separating the pocket from the hardened cement, and retrieving the opened pocket from the bone with the hardened cement remaining in the bone. A primary advantage of this method is allowing a portion of the liquid contained in the cement paste to be expelled out of the pocket, especially when a pressure is applied unto said cement paste before said cement paste is substantially hardened, so that the powder/liquid ratio of said cement paste in said pocket is increased and the strength of the hardened cement is further increased. This further increase in cement strength is especially advantageous for the relatively weak ceramic, calcium-based cement. A typical example can be found in U.S. Pat. No. 7,144,398 B2. Nevertheless, one major difficulty in practicing this method is the accurate control of the selective penetrability (only to liquid) of the pocket, especially during the expansion process, wherein the volume of the pocket continues to increase while the thickness of the pocket continues to decrease.

SUMMARY OF THE INVENTION

The present invention further improves the existing methods for forming a hardened cement in a bone cavity by disclosing an inflatable and expandable balloon with a designed perforation pattern through the membrane of said balloon, wherein the perforation pattern (perforation size, population, and distribution, etc) can be designed and controlled so that the balloon is penetrable to liquid but substantially impenetrable to the powder of the cement paste under an expanded condition. The present invention further discloses a "forced-feeding" method for opening (rupturing) a balloon after its contained cement paste is substantially hardened. A brief description of the present inventive method and device is given below.

The Method

1. A method for treating a bone comprising
    (a) preparing a cement paste from a powder and a liquid, so that said cement paste is injectable through a syringe;
    (b) inserting a perforated balloon into said bone, therein said perforated balloon comprising at least one perforation through the membrane of said balloon; therein the size of said perforation can be controlled so that the balloon is penetrable to liquid but substantially impenetrable to the powder of said cement paste under expanded condition;
    (c) injecting said cement paste into said perforated balloon, wherein said injecting is carried out with a means which is able to be operated outside said bone cavity;
    (d) applying a pressure unto said cement paste before said cement paste is substantially hardened, causing a portion of said liquid contained in said cement paste to be expelled out of said perforated balloon, so that the powder/liquid ratio of said cement paste in said perforated balloon is increased;
    (e) allowing said cement paste at least partially harden in said balloon;
    (f) rupturing said balloon, wherein said rupturing is carried out with a means which is able to be operated outside said bone cavity, and the resulting ruptured balloon is attached to said means;
    (g) separating the resulting ruptured balloon from the hardened cement, wherein said separating is carried out by removing the resulting ruptured balloon from said bone cavity with the hardened cement remaining in said bone cavity.
2. The method in (1) further comprising preparing a minimally invasively percutaneous path for the balloon to be inserted into the bone being treated.
3. The method in (2) further comprising inserting an injection tube into the bone through said percutaneous path, wherein the balloon is connected to or near distal end of said injection tube; through said tube the cement paste is injected into the balloon, wherein the balloon is dilated by the injection of said paste.
4. The perforated balloon in (1b) further comprising multiple perforations through the membrane of said balloon; wherein said multiple perforations comprise a first type of perforations capable of functioning as channels through which a portion of the liquid contained in the cement paste inside the expanded balloon can be expelled out of the balloon.
5. The perforated balloon in (1b) further comprising multiple perforations through the membrane of said balloon; wherein said multiple perforations comprise a second type of perforations designed for being able to function as weak spots, wherein said rupturing in (1f) can preferentially occur at or along said predetermined (designed) weak spots.
6. Said second type of perforations in (5) further comprising at least one perforation array (a "dotted line" of perforations), preferably located at the opposite side to the neck of the balloon (the leading/top portion of the balloon), wherein the rupturing of the balloon can preferentially occur at or along said weak spots when the balloon is dilated and is subjected to an interior or exterior force. Optionally said second type of perforations comprise multiple perforation arrays, preferably located at the opposite side to the neck of the balloon, comprising designed patterns of pores, dents, notches, grooves, cuts, etc. made on the surface of at least a portion of the balloon. Preferably the perforation arrays converge around the apex of the balloon, creating a most weakened area where rupturing cracks would initiate.
7. The first type of perforations in (4) and second type of perforations in (5) and (6) are optionally the same perforations, wherein said same perforations are designed to function as both channels through which a portion of the liquid contained in the cement paste inside the balloon can be expelled out of the balloon under expanded condition, and as weak spots wherein said rupturing in (1f) can preferentially occur at or along said weak spots.
8. Said rupturing in (1f), (5)-(7) is assisted by means of a forced-feeding mechanism, wherein said forced-feeding is characterized by, after said cement paste is substantially hardened, further injecting a biocompatible fluid (water, oil, etc) into the balloon at a flow rate greater than that of the fluid leaking out of the balloon through the perforations to cause said balloon to swell until it ruptures.
9. Said rupturing in (1f), (5)-(7) is assisted by means of a cutting mechanism, wherein said cutting is conducted unto at least a portion of said balloon, preferably located at the opposite side to the neck of the balloon with a cutting means, for example, a thin wire or blade.
10. Said rupturing in (1f), (5)-(7) is assisted by means of a thermal softening/melting mechanism, wherein said thermal softening/melting is conducted with an energy directed by an electrically, thermally or optically conductive wire embedded in at least a portion of said balloon, preferably located at the opposite side to the neck of the balloon.
11. The method in (1) further comprising, prior to inserting a balloon into the bone, creating a cavity and/or restoring at least a portion of height of the bone being treated, wherein the volume of the first bone filler injected into the balloon can be controlled to either avoid further expanding the bone, or to further expand the bone.
12. The balloon is preferably made from an inflatable, preferably inflatable and expandable, polymeric material (PU, rubber, etc), although any other material in any form (fabric, mesh, etc) which may serve the purpose may be used.
13. The sizes of the perforations in (1), (4)-(7) are substantially less than the particle size of the powder in the cement paste so that liquid can be squeezed out but cement powder cannot penetrate through the perforations. Preferably the perforation sizes are less than 10 microns, and more preferably less than 1 micron.

14. Said powder in said cement paste in (1a) is made from a biocompatible material, preferably a biocompatible and bioconductive material, more preferably a biocompatible, bioconductive and bioresorbable material.
15. Optionally a wire or thread can be connected to any part of the balloon, preferably at the opposite side to the neck of the balloon, as a safety device, wherein, in case a portion (piece) of the ruptured balloon is broken off, the broken-off portion can be retrieved by the connected wire/thread independently.
16. The bone being treated is preferably a diseased or fractured vertebral body.

The Device

A. A perforated balloon for entrapping a cement paste for treating a bone until the paste is hardened inside the balloon in a bone cavity; wherein the perforated balloon is adapted to be mounted on an end of an injection tube of a cement paste delivering tool through which the paste is injected into the balloon and the balloon is dilated by the injection of the cement paste; wherein said perforated balloon comprising at least one perforation through the membrane of said balloon; wherein the size of said perforation can be controlled so that the balloon is penetrable to liquid but substantially impenetrable to the powder of said cement paste under expanded condition.

B. The perforated balloon in (A) further comprising multiple perforations through the membrane of said balloon; wherein said multiple perforations comprise a first type of perforations capable of functioning as channels through which a portion of the liquid contained in the cement paste inside the expanded balloon can be expelled out of the balloon.

C. The perforated balloon in (A) further comprising multiple perforations through the membrane of said balloon; wherein said multiple perforations comprise a second type of perforations designed for being able to function as weak spots, wherein said rupturing of the balloon can preferentially occur at or along said predetermined (designed) weak spots.

D. The second type of perforations in (C) further comprising at least one perforation array (a "dotted line" of perforations), preferably located at the opposite side to the neck of the balloon (the leading/top portion of the balloon), wherein said rupturing of the balloon can preferentially occur at or along said weak spots when the balloon is dilated and is subjected to an interior or exterior force. Optionally said second type of perforations comprise multiple perforation arrays, preferably located at the opposite side to the neck of the balloon, comprising designed patterns of pores, dents, notches, grooves, cuts, etc. made on the surface of at least a portion of the balloon. Preferably the perforation arrays converge around the apex of the balloon, creating a most weakened area where rupturing cracks would initiate.

E. The first type of perforations in (B) and second type of perforations in (C) and (D) are optionally the same perforations, wherein said same perforations are designed to function as both channels through which a portion of the liquid contained in the cement paste inside the balloon can be expelled out of the expanded balloon, and as weak spots wherein said rupturing of the balloon can preferentially occur at or along said weak spots.

F. Said rupturing of the balloon in (C)-(E) is assisted by a forced-feeding mechanism, wherein said forced-feeding is characterized by, after said cement paste is substantially hardened, further injecting a biocompatible fluid (water, oil, etc) into the balloon at a flow rate greater than that of the fluid leaking out of the balloon through the perforations to cause said balloon to swell until it ruptures.

G. Said rupturing of the balloon in (C)-(E) is assisted by pulling or twisting the injection tube while pushing the substantially hardened cement by inserting a stylet into the tube while holding the tube after the cement paste is substantially hardened inside the balloon.

H. Said rupturing of the balloon in (C)-(E) is assisted by a cutting mechanism, therein said cutting is conducted unto at least a portion of said balloon, preferably located at the opposite side to the neck of the balloon, with a cutting means, for example, a thin wire or blade.

I. Said rupturing of the balloon in (C)-(E) is assisted by a thermal softening/melting mechanism, therein said thermal softening/melting is conducted with an energy directed by an electrically, thermally or optically conductive wire embedded in at least a portion of said balloon, preferably located at the opposite side to the neck of the balloon.

J. The sizes of the perforations in (A)-(E) are substantially less than the particle size of the powder in the cement paste so that liquid can be squeezed out but cement powder cannot penetrate through the perforations. Preferably the perforation sizes are less than 10 microns, and more preferably less than 1 micron.

K. The balloon membrane preferably has a substantially uniform thickness and a predetermined shape.

L. The balloon is preferably made from an inflatable, preferably inflatable and expandable, polymeric material (PU, rubber, etc), although any other material in any form (fabric, mesh, etc) which may serve the purpose may be used.

M. Said powder in said cement paste is made from a biocompatible material, preferably a biocompatible and bioconductive material, more preferably a biocompatible, bioconductive and bioresorbable material.

O. Said biocompatible material in (M) comprising a calcium-based compound comprising calcium phosphate, calcium sulfate, bioactive glass or their composites.

P. Said cement paste is further doped with a relatively strong and rigid biocompatible phase, such as calcium phosphate particles, calcium sulfate particles, or bioactive glass particles or their composites, for improving strength of said cement.

Q. Said cement paste is further doped with a BMP, a growth factor (e.g., a bone marrow or blood-derived growth factor), or living cells for enhancing bone resorption/healing processes.

R. Optionally a wire or thread can be connected to any part of the balloon, preferably at the opposite side to the neck of the balloon, as a safety device, wherein, in case a portion (piece) of the ruptured balloon is broken off, the broken-off portion can be retrieved by the connected wire/thread independently.

DETAILED DESCRIPTION OF THE INVENTION

As bone cement paste is delivered into a balloon made from elastic material (for example, a polymeric PU), surface tension will be created due to the stretch of the balloon membrane. The pressure differential (ΔP) across membrane is proportional to the surface tension and inversely proportional to the radius of curvature of the balloon:

$$\Delta P = P_b - P_a = \frac{2\gamma}{R} \quad (1)$$

wherein $P_b$ is the pressure inside the balloon, $P_a$ is the pressure outside the balloon, r is the diameter of the perforations, and R is the radius of curvature of the balloon. The static equilibrium between the pressure differential across the membrane and the surface tension sets an ideal stage for cement to solidify. In order to expel air or water trapped originally in the balloon before cement delivery, tiny holes/perforations were made as venting flow passages distributed in the membrane wall. These tiny holes serve two major roles for bone cement delivery, one as the air/water filter and another as the crack initiator for the subsequent balloon rupture.

Figure 1:
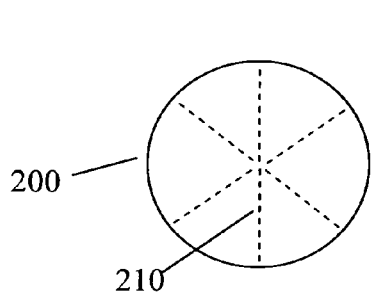
FIG. 1 is a schematic front view of a perforated balloon for entrapping an orthopaedic paste in a bone cavity until the paste is hardened in a bone cavity disclosed in the present invention.
Figure 2:
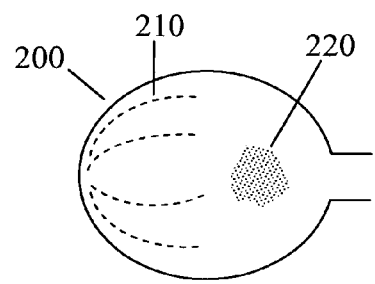
FIG. 2 is a schematic side view of the perforated balloon shown in FIG. 1.

In order for the balloon to be ruptured in a predetermined (designed) manner (pattern) after the cement is hardened, "perforation array" is designed, for example the perforation array 210 shown in FIGS. 1 and 2. The perforation array 210 is used mainly to rupture the inflated balloon 200 with predetermined lines/pattern of breakup, although permeability effect is also provided therein when the pore size is carefully controlled. The perforation array is also designed to keep the entire ruptured balloon to remain attached to the injection tube end after being ruptured. Without this design, it is highly likely that some random pieces of the ruptured balloon are detached from the balloon and left permanently in the bone cavity. Ideally the entire balloon should remain attached to the injection tube after being ruptured and can be entirely withdrawn along with the tube.

The perforation array 210 comprises designed patterns of pores, dents, notches, grooves, cuts, etc. and are made on the surface of at least a portion of the balloon. Such pores, dents, notches, grooves, cuts, etc. can be made by any conventional methods. Preferably, these pores, dents, notches, grooves, cuts, etc. are made at or near the central part of the balloon. Preferably, the "lines of perforation" converge around the apex of the balloon, creating relatively weakened spots where rupturing crack would initiate.

Such parameters as pore size, population, spacing between perforations, number of perforation array, and the array size are to be controlled and optimized to result in a required structural characteristics of the balloon.

Although permeability (draining) effect is provided in the design of the perforation array, in order to more effectively drain water and air out of the balloon as the cement paste is injected to fill the bone cavity, micro-pores 220 can be further incorporated over the surface of the balloon 200. These micro-pores can be distributed randomly or in a designed manner/pattern and will be progressively enlarged as cement mixture is continually delivered into the balloon.

The perforations of the perforation array 210 and the micro-pores 220 of desired diameters and optionally desired distribution (pattern) can be made mechanically (for example, by needle drilling), chemically (for example, by etching/dissolving) or thermally (for example, by focused heat or laser drilling). The perforations/pores can be made on an empty balloon, a balloon still attached onto a substrate mode (for example, a balloon made by dipping a balloon-shaped substrate mode of a desired size and shape in a PU solution), or a pre-expanded balloon with an infilling material.

As perforations/pores are made on a pre-expanded balloon, the infilling material can be any material which can be delivered into and expand the balloon, and removed from the balloon after perforations are made on the expanded balloon. The infilling material is preferably a high-viscosity powder-liquid mixture paste which will not set/harden in a short period of time after mixing (for example, a CaO powder/water mixture). The balloon can be pre-expanded to any desired size whereas perforations are made. One advantage for perforations/pores made on a pre-expanded balloon is its easier control in perforation quality, since the balloon surface is enlarged during expansion.

As a balloon swells to certain critical size, the internal stresses developed in the stretched membrane will reach the balloon fracture stress threshold. The corresponding strain at balloon fracture can be converted into the rupture volume of the balloon. When balloon is filled with any material which expands the balloon to this critical volume, balloon will fracture spontaneously and the fractured balloon membrane will shrink to its zero-stress state size. Balloon extraction can hence be achieved while leaving the solidified cement deployed in the designated bone cavity.

Figure 3:
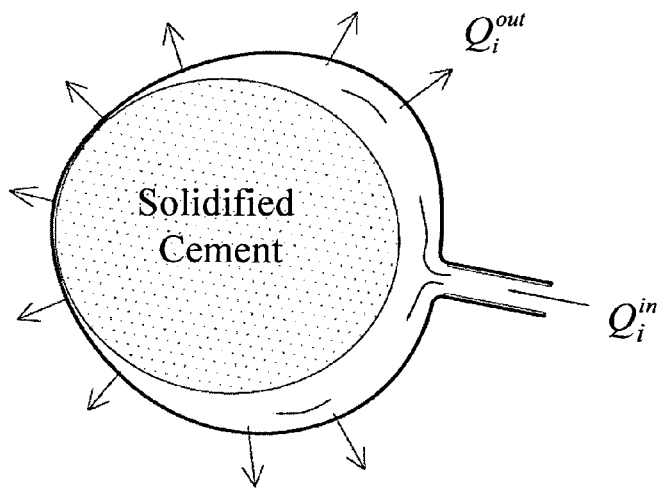
FIG. 3 is a schematic side view of a cement-filled balloon under forced-feeding by fluid.

FIG. 3 shows a cement-filled balloon under forced-feeding by fluid.

As the feeding pressure destroys the initial static equilibrium the solidified cement will be lifted up immediately with an inlet flow passage created around the feeding entrance, followed by a filling of the balloon due to the infused fluid volume. Any fluid, gas or liquid, can be used as the filling material so long as it is biocompatible. These fluid fillers first separate the balloon membrane from the solidified cement surface, greatly reducing the contact friction by generating a layer of fluid buffer. Then a further injection of fluid filler will expand the balloon until balloon rupture is accomplished. According to the mass conservation of fluids, the rate of mass increment contained in the balloon closure is equal to the net mass flux convected through the inflow/outflow tracts:

$$\rho \frac{dV}{dt} = \sum_i \rho Q_i^{in} - \sum_i \rho Q_i^{out} \quad (2)$$

in which, V is the volume and ρ is the density of the fluid while $Q_i^{in}$ and $Q_i^{out}$ are the inflow and outflow volume flowrates, respectively. For the case illustrated in FIG. 3, $Q_i^{in}$ is the forced-feeding influx and $$\sum_i Q_i^{out}$$

is the net outflux contributed by all the leakage flows across the micro-pores and perforations in the membrane wall. So long as the volume flux of the inflow is greater than that of the outflow, the balloon will keep on swelling until it ruptures.

Figure 4:
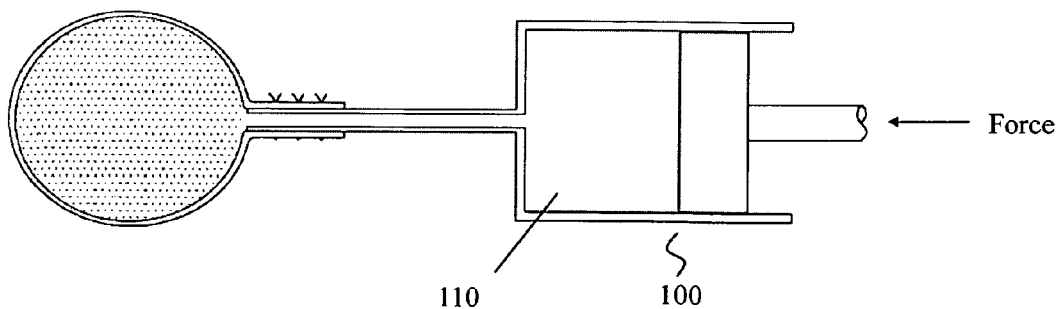
FIG. 4 is a schematic side view showing a representative implementation of forced-feeding by connecting the balloon rear end to a syringe.

FIG. 4 shows a representative implementation by connecting the balloon rear end to a fluid filler such as a syringe 100 having a fluid reservoir 110. Any decrease of the reservoir volume by pushing the syringe 100 from behind, with sufficiently force and speed, may result in a net volume infusion into the balloon. Balloon will rupture as the accumulated fluid mass increases and the resultant membrane stresses reach the rupture threshold value.

To reduce the risk that a portion (especially the leading/top portion) of ruptured balloon (especially for rupture occurring around the belly/equator portion of the balloon) being trapped in the cavity when the ruptured balloon is retrieved from the cavity site, a thread can be connected to any part of the balloon as a safety device. Since the leading/top portion is one that most easily breaks off the balloon during rupture, the thread can be connected (for example, by glue) to such location. In case a portion of ruptured balloon is broken off, the broken-off piece can be retrieved by the connected wire/thread independently.

The invention claimed is:

1. A perforated balloon for forming a hardened orthopaedic paste in a bone comprising a neck portion adapted to be mounted on an end of a tube through which an orthopaedic paste is injected into the perforated balloon; and leaking perforations, wherein said leaking perforations have a size which is penetrable to liquid contained in said orthopaedic paste but substantially impenetrable to powder contained in said orthopaedic paste under an expanded condition of said perforated balloon, in which the improvement comprises a rupture array formed on said perforated balloon for initiating a rupture of said perforated balloon when the perforated balloon is dilated to exceed a critical size and where said rupture array comprises pores, dents, notches, grooves or cuts formed on said perforated balloon, which function as weak spots so that said rupture occurs along at least a portion of said weak spots; and wherein said weak spots form one or more dotted lines.

2. The perforated balloon as defined in claim 1, wherein said rupture array is located in a region opposite to said neck of said perforated balloon.

3. The perforated balloon as defined in claim 2, wherein said weak spots form one dotted line across an apex of the perforated balloon or more doted lines intersect at an apex of the perforated balloon.

4. The perforated balloon as defined in claim 1, wherein said rupture array comprises pores having a size which is penetrable to liquid contained in said orthopaedic paste but substantially impenetrable to powder contained in said orthopaedic paste under an expanded condition of said perforated balloon.

5. The perforated balloon as defined in claim 4, wherein said pores constitutes a portion of said leaking perforations.

6. The perforated balloon as defined in claim 4, wherein said pores constitutes whole said leaking perforations.

7. The perforated balloon as defined in claim 1 further comprising a forced-feeding mechanism connected to the distal end of the tube from the end of the tube on which is mounted the neck portion of the balloon; and a liquid or gas reservoir in said forced-feeding mechanism, wherein the liquid or gas can be injected from the reservoir into the perforated balloon through said tube after the orthopaedic paste hardens in the perforated balloon by applying a force to said forced-feeding mechanism, wherein the perforated balloon is dilated to exceed the critical size by the injection of the liquid or gas.

8. The perforated balloon as defined in claim 7, wherein said forced-feeding mechanism is a syringe.

9. The perforated balloon as defined in claim 2 further comprising a thread attached to said region as a safety device, wherein, in case a portion of the perforated balloon is broken off after the rupture thereof, the broken-off portion can be retrieved from said bone by the attached thread independently.

* * * * *